United States Patent
Zhao

(10) Patent No.: US 10,698,194 B2
(45) Date of Patent: Jun. 30, 2020

(54) OPTICAL SYSTEM OF A STEREO VIDEO ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/901,306

(22) Filed: Feb. 21, 2018

(65) Prior Publication Data

US 2018/0180868 A1 Jun. 28, 2018

Related U.S. Application Data

(63) Continuation of application No. PCT/EP2016/070369, filed on Aug. 30, 2016.

(30) Foreign Application Priority Data

Sep. 7, 2015 (DE) .......................... 10 2015 217 079

(51) Int. Cl.
*A61B 1/00* (2006.01)
*G02B 23/24* (2006.01)
*A61B 1/002* (2006.01)

(52) U.S. Cl.
CPC .......... *G02B 23/2415* (2013.01); *A61B 1/002* (2013.01); *A61B 1/00096* (2013.01);
(Continued)

(58) Field of Classification Search
CPC ................................................. A61B 1/00193
(Continued)

(56) References Cited

U.S. PATENT DOCUMENTS 4,702,571 A * 10/1987 Barber ..................... G02B 6/06
359/377
5,543,962 A 8/1996 Kitajima
(Continued)

FOREIGN PATENT DOCUMENTS

CN 102597871 A 7/2012
CN 103119495 A 5/2013
(Continued)

OTHER PUBLICATIONS

International Search Report dated Nov. 2, 2016 issued in PCT/EP2016/070369.
(Continued)

*Primary Examiner* — Jeffery A Williams
(74) *Attorney, Agent, or Firm* — Scully, Scott, Murphy & Presser, P.C.

(57) ABSTRACT

An optical system including: a sideways-viewing, distal optical assembly including an entry lens, a deflecting unit configured as a prism unit, and an exit lens on a common optical axis; a proximal optical assembly including left and right lens system channels, wherein the right and left lens system channels are identically configured and parallel to each other and each having an optical axis; and a prism unit between the distal optical assembly and the proximal optical assembly, the prism unit couples a left beam path exiting the exit lens into the left lens system channel and a right beam path exiting the exit lens into the right lens system channel; wherein a second distance between the left and right lens system channels is adjustable, the second distance being in a direction perpendicular to the first and second optical axes of the respective first and second lens system channels.

13 Claims, 6 Drawing Sheets

(52) U.S. Cl.
CPC ...... *A61B 1/00179* (2013.01); *A61B 1/00193* (2013.01); *G02B 23/243* (2013.01); *G02B 23/2453* (2013.01)

(58) Field of Classification Search
USPC .......................................................... 348/45
See application file for complete search history.

(56) References Cited

U.S. PATENT DOCUMENTS

| | | | |
|---|---|---|---|
| 5,588,948 A | | 12/1996 | Takahashi et al. |
| 5,689,365 A | | 11/1997 | Takahashi |
| 5,743,846 A | * | 4/1998 | Takahashi .......... A61B 1/00193 600/111 |
| 5,880,884 A | | 3/1999 | Hauptli |
| 5,976,071 A | * | 11/1999 | Sekiya ............... A61B 1/00193 600/111 |
| 6,139,490 A | | 10/2000 | Breidenthal et al. |
| 2013/0041215 A1 | | 2/2013 | McDowall |
| 2013/0162776 A1 | * | 6/2013 | Noack ................. A61B 1/0008 348/45 |
| 2015/0043065 A1 | | 2/2015 | Hong et al. |
| 2016/0004065 A1 | | 1/2016 | Zobel |
| 2016/0154231 A1 | | 6/2016 | Zhao et al. |

FOREIGN PATENT DOCUMENTS

| | | |
|---|---|---|
| CN | 104020557 A | 9/2014 |
| DE | 3622126 A1 | 3/1987 |
| DE | 4320580 A1 | 12/1993 |
| DE | 102012220051 A1 | 5/2014 |
| DE | 102014107586 A1 | 12/2014 |
| DE | 102013215422 A1 | 2/2015 |
| DE | 102013217449 A1 | 3/2015 |
| JP | H08-056891 A | 3/1996 |
| WO | WO 2014/130547 A1 | 8/2014 |
| WO | 2015/018473 A1 | 2/2015 |

OTHER PUBLICATIONS

Japanese Office Action dated Jul. 23, 2019 in Japanese Patent Application No. 2018-512376.

* cited by examiner

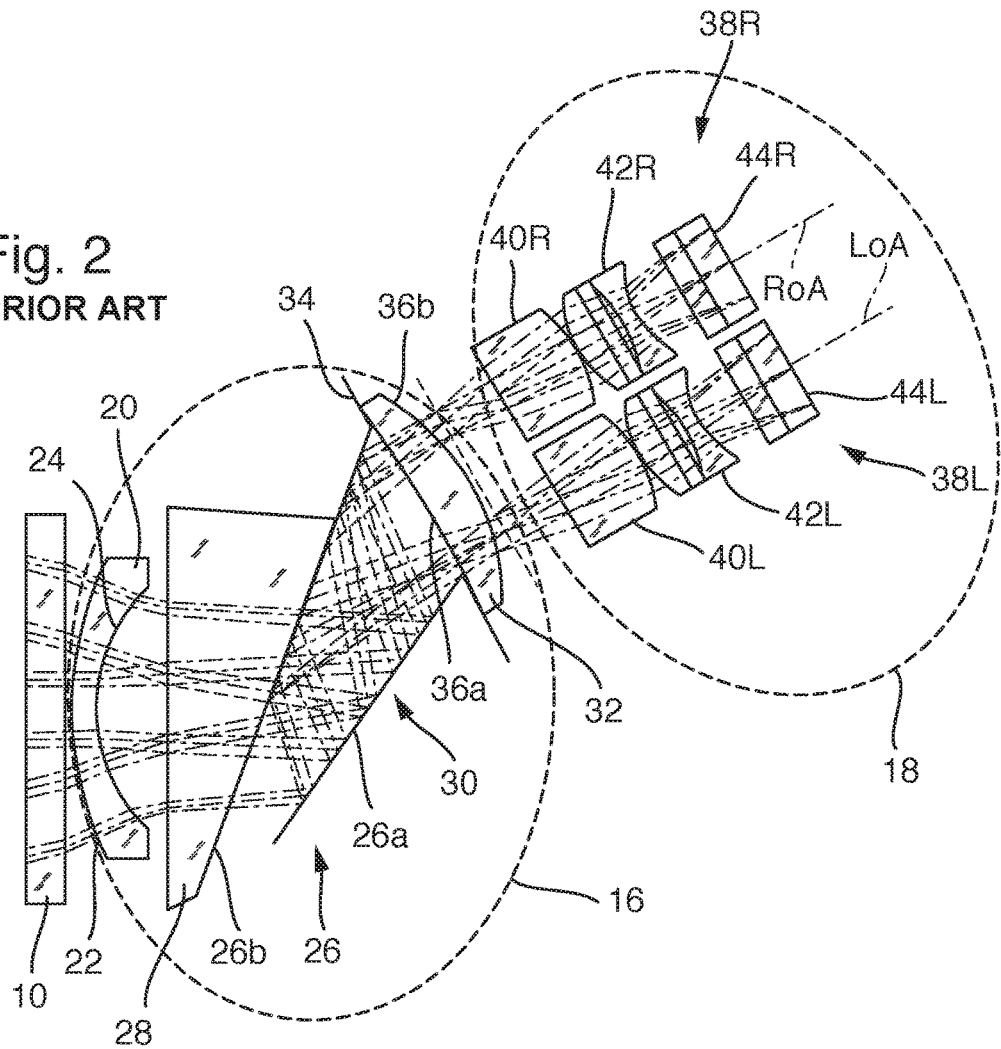

OPTICAL SYSTEM OF A STEREO VIDEO ENDOSCOPE

CROSS-REFERENCE TO RELATED APPLICATION

The present application is a continuation of PCT/EP2016/070369 filed on Aug. 30, 2016, which is based upon and claims the benefit to DE 10 2015 217 079.9 filed on Sep. 7, 2015, the entire contents of each of which are incorporated herein by reference.

BACKGROUND

Field

The present disclosure relates to an optical system of a stereo video endoscope and more particularly relates to a stereo video endoscope with a lateral viewing direction comprising a sideways-viewing, distal optical assembly and a proximal optical assembly, wherein sequentially in a direction of incident light, the distal optical assembly comprises an entry lens, a deflecting unit designed as a prism unit, and an exit lens on a common optical axis, and wherein the proximal optical assembly comprises a left and a right lens system channel, wherein the lens system channels are identically designed and arranged parallel to each other, and each has its own optical axis. Moreover, the present disclose relates to a method for manufacturing such an optical system, and a stereo video endoscope with a lateral viewing direction.

Prior Art

Endoscopes in which light entering at a distal tip of an endoscope shaft is directed through an optical system onto one or more image sensors, are known in different designs. Thus, there are endoscopes with a direct view, a so-called 0° viewing direction, or endoscopes with a lateral viewing direction, which have for example a deviation of 30°, 45° or 70° from the 0° viewing direction. The cited degree numbers indicate the angle between a central viewing axis and the longitudinal axis of the endoscope shaft. Moreover, endoscopes with an adjustable lateral viewing direction are known. With these, the viewing angle, i.e., the deviation from a direct view, is adjustable. Such endoscopes are frequently termed V-DOV (variable direction of view) endoscopes.

Stereo video endoscopes are configured to record a stereoscopic pair of images, or respectively two stereoscopic video channels, in order to provide a 3D-image of the distal examination or surgical field lying before the end of the endoscope shaft. In the case of stereo video endoscopes, the two optical channels are recorded from a slightly different viewing direction. The two viewing directions are offset, or respectively shifted by the stereo base, i.e., the distance between the two viewing directions. A right and left image channel are recorded simultaneously and are made available to a user via especially suitable playback devices, for example on a 3D-screen or via 3D-video-glasses. The user is accordingly enabled to view a 3D-image of an examination or surgical field.

DE 10 2014 107 586 A1 and WO 2014/130 547 A1 disclose a straight view stereo video endoscope in which the beam paths of two lenses spaced by a stereo base are combined by means of a prism unit. The beam path generated in this matter requires less room in the endoscope shaft than the two separate and spaced beam paths of the left and right channel needed for the stereoscopic image. It is also possible to use a single image sensor for imaging.

An optical system of a stereo video endoscope with a lateral viewing direction is known from DE 10 2013 215 422 A1. The system comprises a sideways-viewing, distal optical assembly that is arranged behind the entrance window. This seals the endoscope shaft from the outside. The distal optical assembly sequentially comprises—observed in the light incidence direction—an entrance lens, an optical deflecting unit that is made of a plurality of prisms, and an exit lens. A right and left lens system channel of a proximal optical assembly follow further on the exit lens of the distal optical assembly as observed in the light incidence direction. The two lens system channels each have their own optical axis and are configured to image the left and the right channel on an image sensor in each case.

DE 10 2013 217 449 A1 discloses a prism unit for a stereo video endoscope. With this prism unit, the viewing direction of the stereo video endoscope can be changed about a vertical and horizontal axis of rotation. The two rotational axes are perpendicular on a longitudinal axis of the endoscope shaft. The prism unit comprises a central deflecting unit and two pairs of deflecting prisms, which are respectively arranged on opposite-lying sides of the central deflecting unit.

FIG. 1 shows a simplified perspective representation of an endoscope 2 with a proximal handle 4 and a rigid endoscope shaft 6. A viewing window 10 is located at a distal tip 8 of the endoscope shaft 6. This is followed by a distal section 12 of the endoscope shaft 6. An optical system is arranged in the distal section 12 (not visible in FIG. 1) with which an examination or surgical field lying in front of the distal tip 8 of the endoscope 2 is imaged on imaging sensors (also not shown). In the distal direction, a rotary wheel 14 follows on the handle 4 with which the optical system lying within the interior of the endoscope shaft 6 can be azimuthally rotated.

In a simplified schematic sectional view, FIG. 2 shows an optical system as for example known from DE 10 2013 215 422 A1 by the applicant Olympus Winter & Ibe GmbH, Hamburg. The optical system comprises a sideways-viewing distal optical assembly 16 that is arranged behind the entry window 10. For example, the portrayed optical system can be located in the distal section 12 of the stereo video endoscope 2 shown in FIG. 1. In addition to the distal optical assembly 16, the optical system comprises a proximal optical assembly 18. This can be rotated for example by rotating the rotary wheel 14 in the endoscope shaft 6.

The distal optical assembly 16 comprises an entry lens 20 that for example is designed as an elevated negative meniscus. It comprises a convex outer surface 22 and a concave inner surface 24. The light entering the viewing window 10 from the left side passes through the entry lens 20 and enters a deflecting unit 26 designed as a prism unit. This comprises two prisms with a partially mirrored, or respectively mirrored boundary surface. The light entering at an angle from the side is deflected by the deflecting unit 26 in the direction of a longitudinal axis of the endoscope shaft 6. The deflecting unit 26 comprises a first partially mirrored prism 28 that comprises the partially mirrored boundary surface 26b. Moreover, the deflecting unit 26 comprises another partially mirrored prism 30 which is not shown and comprises the mirrored boundary surface 26a.

Moreover, the distal optical assembly 16 comprises an exit lens 32 that is arranged in the direction of incident light behind an aperture 34, and into which enters the light exiting from the deflecting unit 26. The exit lens 32 is for example designed as a hollow positive meniscus lens. It has a concave entry surface 36a and a convex exit surface 36b. In this regard, the radius of curvature of the concave entry surface 36a is larger than the radius of curvature of the concave exit surface 36b.

After a short length, the light exiting the exit lens 32 reaches the proximal optical assembly 18. This comprises a left lens system channel 38L and a right lens system channel 38R. The two lenses system channels 38L, 38R are designed the same and are arranged parallel to each other. The left optical channel has a left optical axis LoA, and the right optical channel has a right optical axis RoA. The optical axes LoA, RoA are orientated at least approximately parallel to each other. The two lens system channels 38L, 38R each comprise a rod lens 40L, 40R into which the light proceeding from the exit lens 32 of the distal optical assembly 16 first enters. An achromatic lens group 42L, 42R follows both the left and right rod lens 40L, 40R in the direction of incident light. The achromatic lens groups 42L, 42R are each designed as triplets. From these, the light is directed to the left, or respectively right image sensor 44L, 44R so that the examination or surgical field lying before the distal tip 8 of the endoscope shaft 6 is imaged.

Further details on the design of the optical system shown in FIG. 2 can be found in the aforementioned DE 10 2013 215 422 A1.

FIGS. 3a-3c show another optical system of a stereo video endoscope 2 as for example can be found in DE 10 2013 217 449 A 1 by the applicant Olympus Winter & The GmbH, Hamburg. The optical system makes it possible to change the viewing direction of the endoscope 2 about two pivot axes. FIG. 3a shows a schematically simplified perspective view, FIG. 3b shows a schematically simplified side view and FIG. 3c shows a schematically simplified plan view. An identical coordinate cross is added to FIGS. 3a to 3c in order to illustrate the orientation of the shown views relative to each other. The shown coordinate system is accordingly uniform for all views. Its x-axis corresponds for example to a horizontal axis, and its y-axis corresponds for example to a vertical axis. The z-axis then extends in the direction of a longitudinal axis of the endoscope shaft 6.

The shown optical system comprises a prism unit 46 and a proximal optical assembly 18. The latter is designed analogous to the proximal optical assembly 18 described with reference to FIG. 2. In contrast to FIG. 2, FIGS. 3a-3c only shows a left lens group 48L and a right lens group 48R that provide an image to a left and right image sensor 44L, 44R.

The prism unit 46 comprises a left and right entry lens 50L, 50R into which light beams from a left, or respectively right beam path enter. Proceeding from the entry lenses 50L, 50R, the light beams enter into a first prism 52L, 52R. The left entry lens 50L is for example adhered to the first left prism 52L. Likewise, the right entry lens 50R is adhered to the first right prism 52R. Accordingly, the left beam path proceeding from the left entry lens 50L enters into the first left prism 52L and passes from there into a central deflecting prism 54. From the central deflecting prism 54, the left beam path proceeds to enter into the second left prism 56L and via the left exit lens 58L into the left lens system channel 38L of the proximal optical assembly 18. The right beam path proceeding from the first right prism 52R passes via the central deflecting prism 54 into a second right prism 56R. Proceeding therefrom, the right beam path then passes via the right exit lens 58R into the right lens system channel 38R of the proximal optical assembly 18. The central deflecting prism 54 is for example made of two superimposed prisms whose common boundary surface is mirrored on both sides.

The prism unit 46 can pivot about a vertical pivot axis A1, and about a horizontal pivot axis A2. This is serves to change the viewing direction in a horizontal, or respectively vertical direction. Further details on the design of the prism unit 46 as shown in FIGS. 3a-3c can be found in the aforementioned DE 10 2013 217 449 A1.

SUMMARY

An object is to provide an optical system of a stereo video endoscope with a lateral viewing direction, a stereo video endoscope with a lateral viewing direction, and a method for manufacturing an optical system for a stereo video endoscope with a lateral viewing direction with a more flexible design.

Such object can be solved by an optical system of a stereo video endoscope with a lateral viewing direction comprising a sideways-viewing, distal optical assembly and a proximal optical assembly, wherein sequentially in a direction of incident light, the distal optical assembly comprises an entry lens, a deflecting unit designed as a prism unit, and an exit lens on a common optical axis, and wherein the proximal optical assembly comprises a left and a right lens system channel, wherein the lens system channels are identically designed and arranged parallel to each other, and each has its own optical axis, wherein moreover the optical system is developed in that a prism unit is also comprised which is arranged between the distal optical assembly and the proximal optical assembly, wherein the prism unit is configured to couple a left beam path exiting the exit lens of the distal optical assembly into the left lens system channel of the proximal optical assembly, and to couple a right beam path exiting the exit lens of the distal optical assembly into the right lens system channel of the proximal optical assembly, and wherein a second distance between the left and right lens system channel can be adjusted, the second distance being determined in a direction perpendicular to the optical axes of the lens system channels.

Such optical system of the stereo video endoscope can be highly flexible. This flexibility can be achieved by the prism unit being arranged between the distal and proximal optical assembly. The resolution of modern stereo video endoscopes is ever increasing, i.e., their sensors have ever increasing numbers of pixels. It is true that the size of the individual pixels, the so-called pixel size, is decreasing; however, this reduction is unable to compensate for the increasing number of pixels. Consequently, the surface of the image sensor increases as the number of pixels rises. This technical development poses ever new and different requirements on the optical design of stereo video endoscopes. At the same time, the installation space within the endoscope shaft is limited. The prism unit integrated in the optical system makes it possible to flexibly adapt the optical imaging system to sensors of different size.

Accordingly, one and the same optical design can be used for small image sensors as are sufficient for a low image resolution, as well as for large image sensors as are needed for high-resolution imaging systems. This makes it possible to use a large number of equivalent parts, such as for example in different endoscope series. This leads to significantly lower costs for manufacturing and servicing the endoscope.

In the context of the present specification, the second distance between the left and right lens system channel is adjustable. The distance between the optical axis of the left lens system channel and the optical axis of the right lens system channel can be adjustable.

In an embodiment of the optical system, the prism unit comprises a first left prism and a first right prism, a central deflecting prism and a second left prism and second right prism, wherein a left beam path proceeding in the direction of incident light from the exit lens of the distal optical assembly passes through the first left prism, the central deflecting prism and the second left prism, and a right beam path proceeding in the direction of incident light from the exit lens of the distal optical assembly passes through the first right prism, the central deflecting prism and second right prism, and wherein the left beam path proceeding from the second left prism enters the left lens system channel, and the right beam path proceeding from the second right prism enters the right lens system channel.

The second distance between the left and right lens system channel can be adjustable in that a third distance between the second left prism and the central deflecting prism, and between the second right prism and central deflecting prism is adjustable.

A fourth distance between the second prism and a left exit lens, or respectively the second right prism and a right exit lens of the prism unit can be adjustable.

The respective changes of the third and fourth distance can compensate each other. In other words, an increase in the third distance can be associated with a reduction of the fourth distance by the same path length. The same holds true of course for reverse displacement in which the third distance is shortened and the fourth distance can be correspondingly lengthened by the same path length. In other words, the change for example of the fourth distance compensates just the change of the third distance. The optical path from the entry lens of the optical system to the image sensor remains constant with this type of shift, or respectively change. In addition, the optical system accordingly does not change its optical imaging properties. A change in the distance between the two lens system channels therefore does not have any influence on optical imaging. It is therefore possible to adapt the optical system to different size image sensors without changing its imaging properties. Thus, a complicated adaptation or even recalculation of the optical system does not have to be pursued.

According to another embodiment, a first distance between the exit lens of the distal optical assembly and the prism unit can be adjustable. By changing the first distance, it is accordingly possible to compensate for a change in the third distance. In order for the entire optical path length from the entry lens of the optical system to the image system to remain constant in this case as well, the change in the distance can be twice as large as that of the first distance.

A first distance between the exit lens of the distal optical assembly and a first left and a first right prism can be adjustable. In this context, the prism unit can be designed as described below; such as, the prism unit can have a first left prism and a first right prism, a central deflecting prism, as well as a second left prism and a second right prism.

Since the first distance can be changed, it is possible to transport the image information through the prisms of the distal optical assembly without trimming the image. The first distance is thereby reduced, or respectively selected to be very small. If the distance is selected to be larger, or respectively is enlarged, it is possible to increase the stereo angle and thereby reinforce the stereo effect.

In the context of the present specification, the "first distance" is understood to be the distance between the surface of the exit lens (or a middle plane of the exit lens) and a plane in which the entry surfaces of the two prisms extend, i.e., the first left and first right prism, or a left, or respectively right entry lens of the prism unit.

According to another embodiment, the optical system can be configured such that the left lens system channel comprises a left image sensor, and the right lens system channel comprises a right image sensor, wherein the left and the right image sensor can be rotatably mounted.

The images sensors can be pivotable, or respectively rotatable about the respective optical axis of the left, or respectively right lens system channel. Alternatively, the sensors can be pivotable about an axis that runs parallel to the respective optical axis. Pivotably mounted image sensors make it possible to always provide an upright image without having to numerically perform an image correction. This holds true, for example, when the viewing direction of the endoscope changes, when the distal optical assembly is rotated relative to the proximal optical assembly, or respectively relative to the prism system.

Moreover, the prisms of the prism units can be cemented to each other. If the prisms are cemented directly to each other, it becomes superfluous to accommodate the prisms in corresponding holders. Such design of the prism unit is stable and simplified.

Moreover, the distal optical assembly can be pivotable relative to the prism unit. As such, it is possible to change the lateral viewing direction in regard to a so-called polar angle. The viewing direction of the endoscope can be changed without the shaft of the endoscope itself having to rotate.

Such object can also be solved by a stereo video endoscope with a lateral viewing direction that comprises an optical system according to one or more of the aforementioned embodiments.

The same or similar advantages apply to the stereo video endoscope as were previously mentioned with respect to the optical system.

Such object can also be solved by a method for manufacturing an optical system for a stereo video endoscope with a lateral viewing direction, wherein the optical system comprises a sideways-viewing, distal optical assembly and a proximal optical assembly, and wherein sequentially in a direction of incident light, the distal optical assembly comprises an entry lens, a deflecting unit designed as a prism unit, and an exit lens on a common optical axis, and wherein the proximal optical assembly comprises a left and a right lens system channel, wherein the lens system channels are identically designed and arranged parallel to each other, and each has its own optical axis, wherein the method is further developed in that the optical system moreover comprises a prism unit which is arranged between the distal optical assembly and the proximal optical assembly, wherein the prism unit is configured to couple a left beam path exiting the exit lens of the distal optical assembly into the left lens system channel of the proximal optical assembly, and to couple a right beam path exiting the exit lens of the distal optical assembly into the right lens system channel of the proximal optical assembly, and wherein a second distance between the left and right lens system channel is adjusted, the second distance being determined in a direction perpendicular to the optical axes of the lens system channels.

A change or even a recalculation of the imaging properties does not have to be associated with such an adaptation. The adaptation of this distance permits an adaptation of the stereo video endoscope to be manufactured to image sensors of different size.

The same or similar advantages apply to the method for manufacturing an optical system as were previously mentioned with respect to the optical system of a stereo video endoscope.

In such method, the prism unit can comprise a left first prism and a right first prism, a central deflecting prism and a left second prism and right second prism, wherein a left beam path proceeding in the direction of incident light from the exit lens of the distal optical assembly passes through the first left prism, the central deflecting prism and the second left prism, and a right beam path proceeding in the direction of incident light from the exit lens of the distal optical assembly passes through the first right prism, the central deflecting prism and second right prism, and wherein the left beam path proceeding from the second left prism enters the left lens system channel, and the right beam path proceeding from the second right prism enters the right lens system channel.

In this regard, the second distance between the left and right lens system channel can be adjusted in that a third distance between the second left prism and the central deflecting prism, and between the second right prism and central deflecting prism can be adjusted.

Moreover, a first distance between the exit lens of the distal optical assembly and the prism unit can be changed to compensate for a change in the length of the beam path arising from the adjustment of the second distance, wherein, for example, the first distance can be changed by twice the amount as the third distance.

Moreover, a fourth distance can be respectively changed that is measured between the second left prism and a left exit lens, or respectively between the second right prism and a right exit lens of the prism unit, wherein the fourth distance can be respectively changed by the same amount as the third distance.

In other words, the change of the third distance can be compensated by a corresponding change in the opposite direction of the fourth distance. If the third distance accordingly increases by a certain amount, the fourth distance is correspondingly reduced by this amount. The same also holds true of course for the converse instance in which the third distance is reduced by a certain amount, and the fourth distance is increased. The corresponding amount is naturally added to the fourth distance.

BRIEF DESCRIPTION OF THE DRAWINGS

Further features will become apparent from the description of embodiments together with the claims and the included drawings. Embodiments can fulfill individual characteristics or a combination of several characteristics.

The embodiments are described below, without restricting the general idea, based on exemplary embodiments in reference to the drawings, wherein reference is made expressly to the drawings with regard to the disclosure of all details that are not explained in greater detail in the text. In the following:

FIG. 2 illustrates an optical system according to prior art in a simplified schematic sectional view.

In the drawings, the same or similar types of elements and/or parts are provided with the same reference numbers so that a re-introduction is omitted.

DETAILED DESCRIPTION

Figure 4:
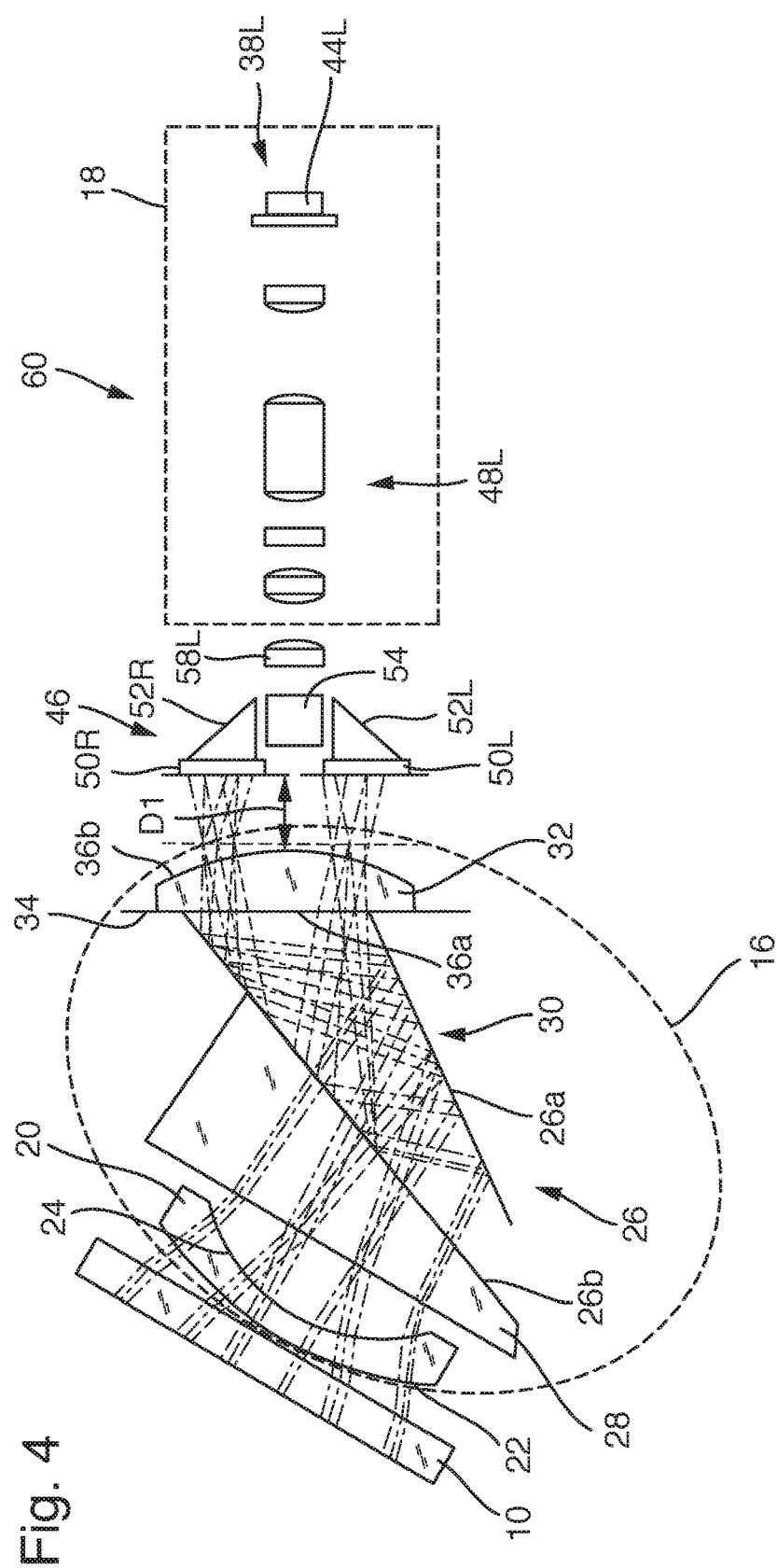
FIG. 4 illustrates an optical system of a stereo video endoscope according to an exemplary embodiment in a simplified schematic sectional view.

FIG. 4 shows an optical system 60 of a stereo video endoscope 2 according to an exemplary embodiment in a simplified schematic sectional view. The portrayed optical system 60 is for example integrated in the distal section 12 of the stereo video endoscope 2 shown in FIG. 1 In order to realize a stereo video endoscope 2 with a lateral viewing direction according to an exemplary embodiment.

The optical system 60 comprises a sideways-viewing distal optical assembly 16 that has already been described with regard to FIG. 2. This is arranged behind the entry window 10 of the stereo video endoscope 2. Moreover, the optical system 60 comprises a proximal optical assembly 18 as has already been described in association with FIG. 2, as well is in association with FIGS. 3a-3c. The corresponding parts are provided with identical reference numbers. FIG. 4 shows an example of the left lens system channel 38L of the optical assembly 18, which can be configured as shown in FIGS. 2 and 3a-3c.

The optical system 60 moreover comprises a prism unit 46 that is arranged between the distal optical assembly 16 and proximal optical assembly 18. The prism unit 46 can be configured as described with reference to FIGS. 3a-3c. However, the pivotability about axes A1 and A2 is omitted. The prism unit 46 is configured to couple the left beam bundle exiting the exit lens 32 of the distal optical assembly 16 into the left lens system channel 38L of the proximal optical assembly 18, and furthermore to couple the right beam bundle exiting the exit lens 32 of the distal optical assembly 16 into the right lens system channel 38R of the proximal optical assembly 18. The representation of the prism unit 46 in FIG. 4 substantially corresponds to the representation in FIG. 3c, wherein however due to the sectional view, the central deflecting prism 54 is portrayed, and not the left prism 56L visible in the side view in FIG. 3c.

The optical system 60 is configured in that a second distance D2 can be set and adjusted that is between the left and right lens system channel 38L, 38R in a direction perpendicular to the optical axes LoA, RoA of the lens system channels 38L, 38R. The second distance D2 is portrayed for the sake of illustration in FIG. 3b as well. This second adjustability makes it possible to adapt the optical system 60 to different size image sensors 44L, 44R. In other words, it is possible to use one and the same optical design both for smaller image sensors 44L, 44R (for example with a small diagonal) with a reduced image resolution, and also for large image sensors (with a larger diagonal). The image sensors are for example CDD or CMOS sensors. Whereas smaller sensors with a reduced resolution or number of pixels are economical, large sensors with significantly more pixels have the better resolution. Given their significantly large light-sensitive surface, they are suitable for high-resolution imaging systems.

A change in the second distance D2 causes a change in the overall length of the beam path. To compensate for this, the optical system 60 is configured so that a first distance D1 can be set between the exit lens 32 of the distal optical assembly 16 and the prism unit 46.

The first distance D1 is for example measured between a plane in which the entry lenses 50L, 50R prism units 46 extend, and a plane in which the exit lens 32 of the distal optical assembly 16 extends. This adjustability makes it possible to transport the image information through the prisms 28, 30 of the distal optical assembly 16 without image clipping. For this, the first distance D1 is selected to be rather small or slight. If the first distance D1 is contrastingly selected to be large, this increases the stereo angle and hence the stereo effect as well.

In this regard, the change in the first distance in D1 can be selected to be twice as large as the change in the second distance D2.

The second distance D2 is adapted without the optical image properties of the optical system 60 changing. This will be explained with reference to FIGS. 5a to 5c that each show a schematically simplified detailed view of the optical system 60.

The second distance in D2 between the left and right lens system channel 38L, 38R can be measured between the left optical axis LoA of the left lens system channel 38L and the right optical axis RoA of the right lens system channel 38R. The second distance D2 is changed by changing a third distance D3 between the left prism 56L and the central deflecting prism 54, and between the second right prism 56R and the central deflecting prism 54. At the same time, a fourth distance D4 can be changed between the second left prism 56L and the left exit lens 58L, and between the second right prism 56R and the right exit lens 58R of the prism unit 46.

Figure 5C:
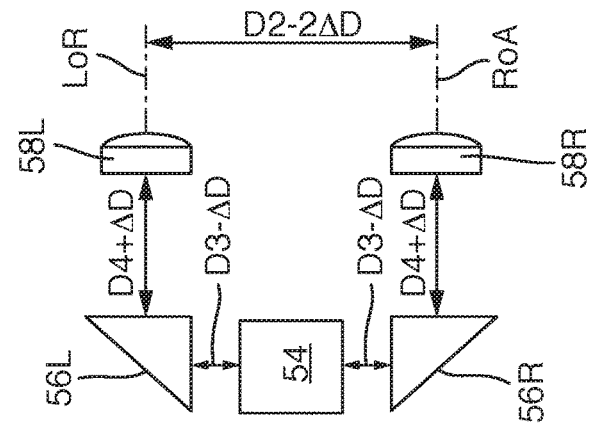
FIGS. 5a-5c illustrate different versions a) to c) of the system of FIG. 4 in a schematically simplified detailed view.
Figure 5B:
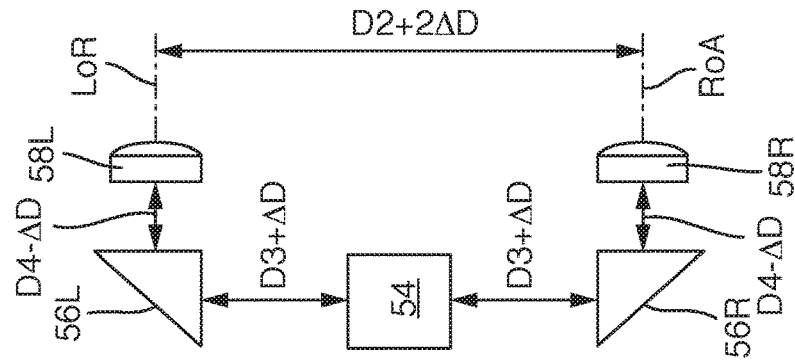
Figure 5A:
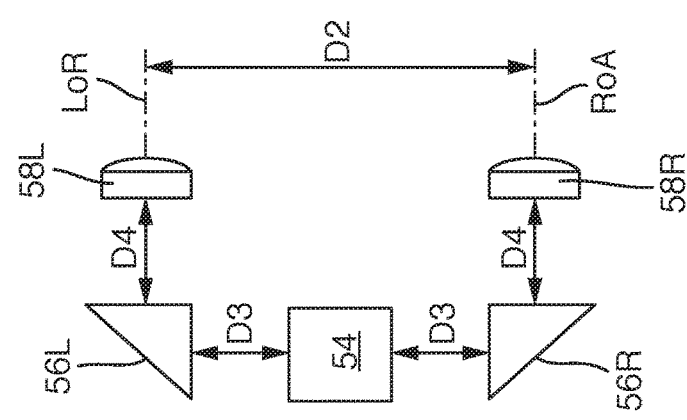

FIG. 5a shows an assumed starting situation. The third distance is greater in FIG. 5b by the amount ΔD. Correspondingly, the fourth distance D4 is lesser by the amount ΔD. Consequently, the second distance D2 between the lens system channels 38L, 38R is greater by the amount 2*ΔD. FIG. 5c shows the converse instance in which the third distance D3 is lesser by the amount ΔD. Correspondingly, the fourth distance D4 is greater by the amount ΔD. Consequently, the second distance D2 between the lens two system channels 38L, 38R is lesser by the amount 2ΔD.

By varying the third and fourth distance D3, D4 it is possible to flexibly adjust the second distance D2 between the two lens system channels 38L, 38R to the size of the image sensors 44L, 44R.

Figure 6A:
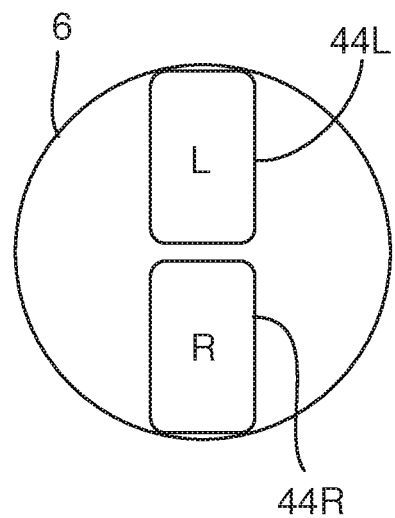
FIGS. 6a, 6b illustrate a schematically simplified sketched arrangement of two image sensors in an endoscope shaft.
Figure 6B:
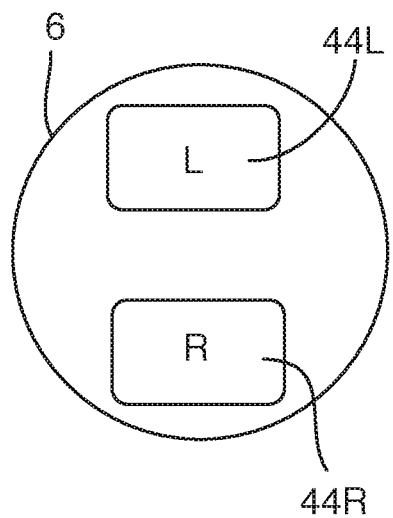

FIGS. 6a and 6b show a schematically simplified view of the arrangement of the left and right image sensor 44L, 44R in the endoscope shaft 6. Whereas FIG. 6a shows the arrangement of the two image sensors 44L, 44R as an example for a landscape format, FIG. 6b shows of the arrangement of the two image sensors 44L, 44R for a portrait format.

Figure 1:
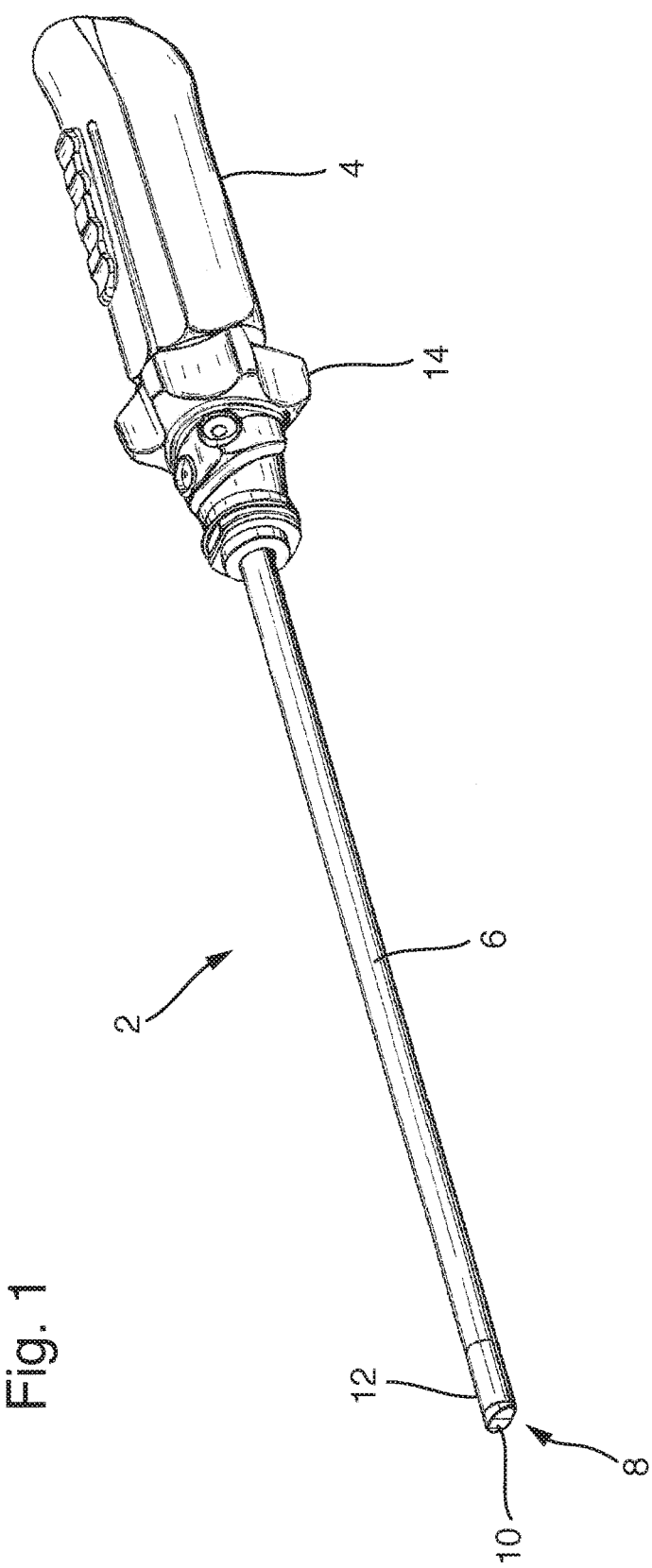
FIG. 1 illustrates a stereo video endoscope in a simplified perspective representation.
Figure 3A:
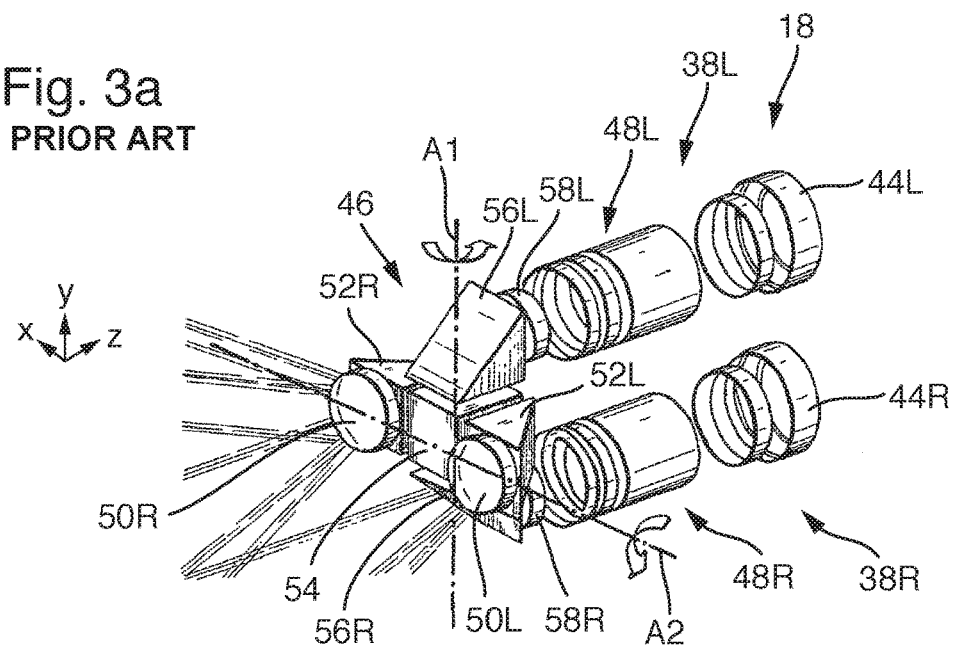
FIGS. 3a-3c illustrate an optical system of a stereo video endoscope with an adjustable viewing direction according to the prior art in a schematically perspective view (FIG. 3a), a simplified side view (FIG. 3b) and a simplified plan view (FIG. 3c)
Figure 3B:
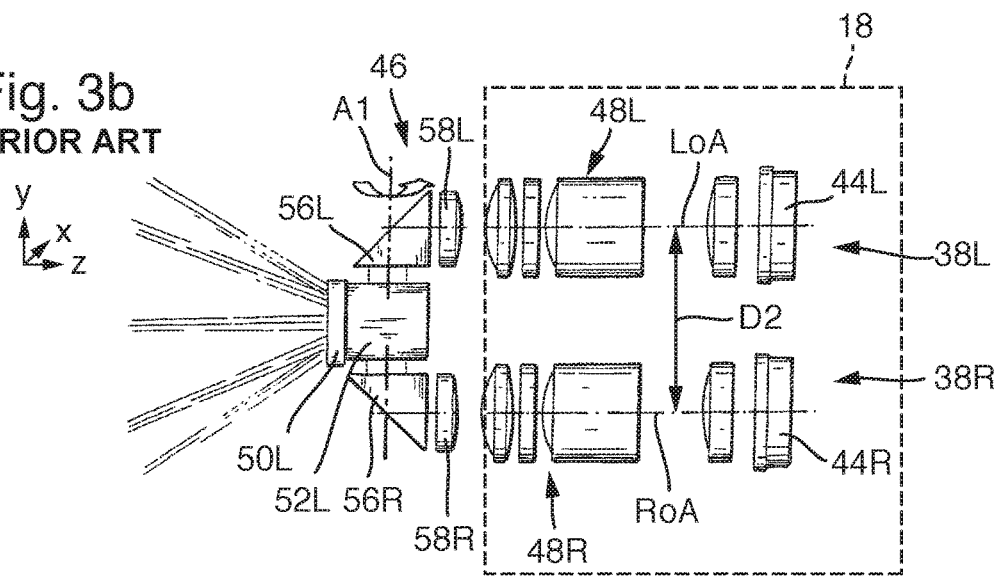
Figure 3C:
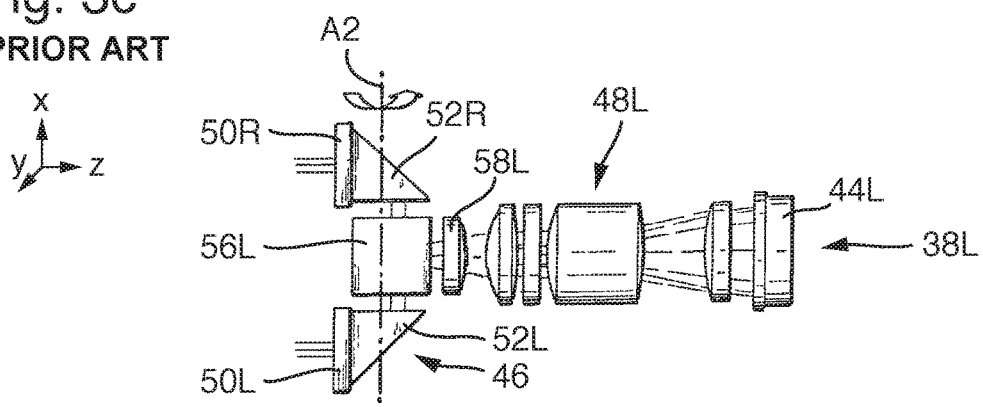

According to a method for manufacturing an optical system 60 as shown for example in FIG. 4 and which is suitable for a stereo video endoscope with a lateral viewing direction as shown for example in FIG. 1, a prism unit 48 is arranged between the distal optical assembly 16 and a proximal optical assembly 18 as is known for example from FIGS. 2 and 3a-3c. Depending on the size of the employed image sensors 44L, 44R, the second distance D2 between the left and right lens system channel 38L, 38R is adapted by changing the third and fourth distance D3, D4, as explained in FIGS. 5a-5c. This adaptation can be carried out without the optical properties of the optical system 60 changing.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Stereo video endoscope
4 Handle
6 Endoscope shaft
8 Distal tip
10 Viewing window
12 Distal section
14 Rotary wheel
16 Distal optical assembly
18 Proximal optical assembly
20 Entry lens
22 Outer surface
24 Inner surface
26 Deflecting unit
26a, 26b Boundary surface
28 Partially mirrored prism
30 Additional partially mirrored prism
32 Exit lens
34 Aperture
36a Concave entry surface
36b Concave exit surface
38L Left lens system channel
38R Right lens system channel
40L, 40R Rod lens
42L, 42R Achromatic lens group
44L, 44R Image sensor
46 Prism unit
48L Left lens group
48R Right lens group
50L Left entry lens
50R Right entry lens
52L First left prism
52R First right prism
54 Central deflecting prisms
52L Second left prism
52L Second right prism
58L Left exit lens
58R Right exit lens
60 Optical system
LoA Left optical axis
RoA Right optical axis
A1 Vertical pivot axis
A2 Horizontal pivot axis
D1 First distance
D2 Second distance of the lens system channels
D3 Third distance
D4 Fourth distance

What is claimed is:

1. An optical system of a stereo video endoscope with a lateral viewing direction comprising:
a sideways-viewing, distal optical assembly, wherein sequentially in a direction of incident light, the distal optical assembly comprises an entry lens, a deflecting unit configured as a prism unit, and an exit lens on a common optical axis;
a proximal optical assembly, wherein the proximal optical assembly comprises a left and a right lens system channel, wherein the right and left lens system channels are identically configured and arranged parallel to each other, and the right lens system channel has a right optical axis and the left lens system channel has a left optical axis; and a prism unit arranged between the distal optical assembly and the proximal optical assembly, wherein the prism unit is configured to couple a left beam path exiting the exit lens of the distal optical assembly into the left lens system channel of the proximal optical assembly and to couple a right beam path exiting the exit lens of the distal optical assembly into the right lens system channel of the proximal optical assembly;

wherein a second distance between the left and the right lens system channels is adjustable, the second distance being in a direction perpendicular to the first and second optical axes of the respective first and second lens system channels.

2. The optical system according to claim 1, wherein the prism unit arranged between the distal optical assembly and the proximal optical assembly comprises:

a first left prism, a first right prism, a central deflecting prism, a second left prism and second right prism;

wherein the left beam path proceeding in the direction of incident light from the exit lens of the distal optical assembly passes through the first left prism, the central deflecting prism and the second left prism, and the right beam path proceeding in the direction of incident light from the exit lens of the distal optical assembly, passes through the first right prism, the central deflecting prism and second right prism, and wherein the left beam path proceeding from the second left prism enters the left lens system channel, and the right beam path proceeding from the second right prism enters the right lens system channel.

3. The optical system according to claim 2, wherein the second distance between the left and right lens system channels is adjustable in that a third distance between the second left prism and the central deflecting prism, and between the second right prism and the central deflecting prism is adjustable.

4. The optical system according to claim 3, wherein a first distance can be adjusted that is between the exit lens of the distal optical assembly and the prism unit arranged between the distal optical assembly and the proximal optical assembly, and/or a fourth distance can be changed that is between the second left prism and a left exit lens of the prism unit, or the second right prism and a right exit lens of the prism unit.

5. The optical system according to claim 1, wherein the left lens system channel comprises a left image sensor, and the right lens system channel comprises a right image sensor.

6. The optical system according to claim 5, wherein the left image sensor and the right image sensor are rotatably mounted.

7. The optical system according to claim 2, wherein the first left prism, the first right prism, the central deflecting prism, the second left prism and the second right prism of the prism unit are cemented to each other.

8. A stereo video endoscope with a lateral viewing direction comprising the optical system according to claim 1.

9. A method for manufacturing the optical system of claim 1, the method comprising adjusting the second distance in a direction perpendicular to the optical axes of the lens system channels.

10. A method for manufacturing the optical system of claim 2, the method comprising adjusting the second distance between the left lens system channel and the right lens system channel by adjusting a third distance between the second left prism and the central deflecting prism and between the second right prism and the central deflecting prism.

11. The method according to claim 10, comprising changing a first distance between the exit lens of the distal optical assembly and the prism unit to compensate for a change in a length of the beam path arising from the adjustment of the second distance.

12. The method according to claim 11, wherein the changing of first distance comprises changing the first distance by twice the amount as the third distance.

13. The method according to claim 10, comprising changing a fourth distance that is measured between the second left prism and a left exit lens, or between the second right prism and a right exit lens of the prism unit, wherein the fourth distance is changed by the same amount as the third distance.

* * * * *